United States Patent
Pantini

(10) Patent No.: US 7,189,408 B2
(45) Date of Patent: *Mar. 13, 2007

(54) COSMETIC COMPOSITIONS

(75) Inventor: Giovanni Pantini, Milan (IT)

(73) Assignee: Solvay Solexis, S.p.A., Milan (IT)

( * ) Notice: Subject to any disclaimer, the term of this patent is extended or adjusted under 35 U.S.C. 154(b) by 341 days.

This patent is subject to a terminal disclaimer.

(21) Appl. No.: 10/767,189

(22) Filed: Jan. 30, 2004

(65) Prior Publication Data

US 2004/0185026 A1    Sep. 23, 2004

Related U.S. Application Data

(62) Division of application No. 09/631,879, filed on Aug. 2, 2000, now Pat. No. 6,699,485.

(30) Foreign Application Priority Data

Aug. 4, 1999 (IT) .............................. MI99A1754

(51) Int. Cl.
  A61K 8/55   (2006.01)
  A61K 31/075 (2006.01)
  A61K 31/755 (2006.01)
(52) U.S. Cl. ...................................... 424/401; 514/129
(58) Field of Classification Search ................ 424/401; 514/129

See application file for complete search history.

(56) References Cited

U.S. PATENT DOCUMENTS

| | | | |
|---|---|---|---|
| 3,665,041 A | 5/1972 | Sianesi et al. |
| 3,715,378 A | 2/1973 | Sianesi et al. |
| 3,810,874 A | 5/1974 | Mitsch et al. |
| 4,536,444 A | 8/1985 | Sumiya et al. |
| 4,803,067 A | 2/1989 | Brunetta et al. |
| 5,093,023 A | 3/1992 | Pantini et al. |
| 5,612,043 A | 3/1997 | Deprez et al. |

FOREIGN PATENT DOCUMENTS

| | | |
|---|---|---|
| EP | 0 148 482 A2 | 7/1985 |
| EP | 0 196 904 A2 | 10/1986 |
| EP | 0 239 123 A2 | 9/1987 |
| EP | 0 355 848 A2 | 2/1990 |
| EP | 0 355 848 B1 | 2/1990 |
| EP | 0 390 206 A2 | 10/1990 |
| EP | 0 390 206 B1 | 10/1990 |
| EP | 0 890 356 A2 | 1/1999 |
| JP | 04225075 | 8/1992 |
| JP | 09 111 286 | 10/1995 |

Primary Examiner—Johann R. Richter
Assistant Examiner—James H. Alstrum-Acevedo
(74) Attorney, Agent, or Firm—Arent Fox PLLC

(57) ABSTRACT

Base compositions (premix) comprising the following components:
A) a perfluoropolyether phosphate;
B) a solvent;
C) water.

18 Claims, No Drawings

COSMETIC COMPOSITIONS

This application is a divisional application which claims the benefit of application Ser. No. 09/631,879, filed Aug. 2, 2000, now U.S. Pat. No. 6,699,485. The disclosure of the prior application is hereby incorporated herein by reference in its entirety.

The present invention relates to stable, monophasic concentrated compositions containing (per)fluoropolyethers, which are diluted with carriers and excipients in order to be used in the product field for personal care, specifically cosmetic and toilet preparations.

In particular the formulations of the present invention contain functionalized (per)fluoropolyethers, capable to confer improved protective hydro/oil-repellence properties to the formulation itself. The monophasic formulations of the present invention can be used, after dilution, as cosmetic products for the skin and hair protection towards irritating agents (acids, bases, solvents, detergents) and allergens.

It is well known in the prior art that (per)fluoropolyethers due to their hydro- and oil-repellence and high filmogenic property are very good protective agents towards both hydrophilic and lipophilic irritating agents.

It is also known that it is not possible to use (per) fluoropolyethers as such for the personal care and hygiene and that said compounds must be carried in suitable formulations for topic use in order to advantageously utilize the above mentioned properties of (per)fluoropolyethers.

The (per)fluoropolyether incorporation in polyphase systems in particular under the form of thri-phase emulsions (oil/water/PFPE), used as creams and lotions for skin hydration and protection, is well known. See for example the patents in the name of the Applicant EP 196,904, EP 355,848, EP 390,206. The latter relates to the preparation of concentrated compositions of (per)fluoropolyethers in glycerine in order to facilitate their incorporation in aqueous monophasic systems.

The (per)fluoropolyethers used in these patents have perfluoroalkyl end groups, which therefore are not reactive end groups.

The drawback of polyphase systems resides in that they require the presence of two essential components: mineral oils (vegetable, animal or synthetic) and emulsifiers (surfactants). The properties of both these components negatively affect the hydro-repellent and/or oil-repellent action of (per)fluoropolyethers having perfluoroalkyl end groups. Therefore in the thri-phase systems of the prior art the hydro- and oil-repellent properties of (per)fluoropolyethers having perfluoroalkyl end groups are reduced.

Also in (per)fluoropolyether systems with glycerine good hydro-repellence values are not obtained.

The thri-phase emulsions are the carrier by which according to the prior art, it is possible to use the above mentioned properties of (per)fluoropolyethers, other systems for formulating compositions having a topic use containing (per) fluoropolyethers, for instance monophase water-based compositions having hydro- and oil-repellent properties, being not available.

The need was felt to have available monophase systems based on perfluoropolyethers having improved hydro- and oil repellence properties with respect to the known polyphase systems.

The Applicant has surprisingly and unexpectedly found monophase concentrated compositions containing functionalized (per)fluoropolyethers, said compositions dilutable with suitable carriers and excipients, in order to obtain products for the personal care, in particular cosmetic and toilet preparations, said cosmetic preparations having a combination of hydro- and oil-repellence properties clearly superior to those of the above described polyphase systems and even superior to those of the pure (per)fluoropolyethers.

An object of the present invention are therefore concentrated compositions comprising the following components:

A) a (per)fluoropolyether phosphate of general formula:

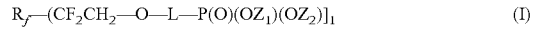

$$R_f\text{—}(CF_2CH_2\text{—}O\text{—}L\text{—}P(O)(OZ_1)(OZ_2))_l \qquad (I)$$

wherein l=1 or 2;

L is a bivalent linking group, preferably of the $(CHR_1CHR_2O)_n$ type wherein $R_1$, $R_2$ equal to or different from each other are selected from H, $CH_3$; n is an integer in the range 1–50, preferably 1–6;

$Z_1$ equal to or different from $Z_2$ selected from H, alkaline or ammonium cation, di- or tri-alkanolammonium cation wherein alkanol comprises from 1 to 20 C atoms, preferably 1–4 C atoms, di- or tri- or tetra-alkylammonium cation wherein alkyl comprises from 1 to 20 C atoms, preferably 1–4 C atoms, or $R_f\text{—}CF_2CH_2\text{—}O\text{—}L\text{—}$;

$R_f$ is a (per)fluoropolyether chain comprising repeating units selected from one or more of the following ones:
a) $\text{—}(C_3F_6O)\text{—}$;
b) $\text{—}(CF_2CF_2O)\text{—}$;
c) $\text{—}(CFL_0O)\text{—}$, wherein $L_0=\text{—}F$, $\text{—}CF_3$;
d) $\text{—}(CF_2(CF_2)_{z'}CF_2O)\text{—}$, wherein z' is an integer 1 or 2;
e) $\text{—}CH_2CF_2CF_2O\text{—}$;

when $R_f$ is monofunctional (l=1), an end group is of the perfluoroalkyl type such as for example $CF_3O$, $C_2F_5O$, $C_3F_7O$; optionally a fluorine atom in the perfluoroalkyl end groups can be substituted by a chlorine or hydrogen atom; examples of these end groups are $Cl(C_3F_6)O$, $H(C_3F_6O)$;

B) a solvent selected from the following ones: linear or branched when possible alcohols, from 2 to 3 carbon atoms and their methyl ethers; linear or branched glycols from 2 to 6 carbon atoms or linear or branched mono alkylethers wherein the alkyl group ranges from 1 to 4 carbon atoms; dimethoxymethane, known as methylal, acetone;

C) water.

The preferred compound of general formula (I) is the one wherein $Z_1$ and $Z_2$ are different from $R_f\text{—}CF_2CH_2\text{—}O\text{—}L\text{—}$; preferably $Z_1=Z_2=H$ and in formula (I) l=2.

In particular, $R_f$ is of perfluoropolyether type and it has preferably one of the following structures:

1) $\text{—}(CF_2O)_a\text{—}(CF_2CF_2O)_b\text{—}$ with b/a in the range 0.3–10, extremes included, a being an integer different from 0;

2) $\text{—}(CF_2\text{—}(CF_2)_{z'}\text{—}CF_2O)_b\text{—}$ wherein z' is an integer equal to 1 or 2;

3) $\text{—}(C_3F_6O)_r\text{—}(C_2F_4O)_b\text{—}(CFL_0O)_t\text{—}$, with r/b=0.5–2.0 (r+b)/t=10–30, b and t being integers different from 0;

4) $\text{—}(OC_3F_6)_r\text{—}(CFL_0O)_t\text{—}OCF_2\text{—}R'_f\text{—}CF_2O\text{—}(C_3F_6O)_r\text{—}(CFL_0O)_t\text{—}$ 5) $\text{—}(CF_2CF_2CH_2O)_q\text{—}R'_f\text{—}O\text{—}(CH_2CF_2CF_2O)_q\text{—}$ wherein:

$R'_f$ is a fluoroalkylene group from 1 to 4 carbon atoms;

$L_0$ is selected between F, $CF_3$;

B) $\text{—}(C_3F_6O)_r\text{—}OCF_2\text{—}R'_f\text{—}CF_2O\text{—}(C_3F_6O)_r\text{—}$ wherein in said formulas:

$\text{—}(C_3F_6O)\text{—}$ can represent units of formula:

$\text{—}(CF(CF_3)CF_2O)\text{—}$ and/or $\text{—}(CF_2\text{—}CF(CF_3)O)\text{—}$ a, b, b', q', r, t, are integers, whose sum is such that $R_f$ has number average molecular
weight $\overline{M}_n$ values in the range of about 300 and about 5,000, and preferably in the range 800–2,500.

The preferred (per)fluoropolyether chain $R_f$ is selected from the following structures: from the bifunctional ones (1=2):
—(CF$_2$O)$_a$—(CF$_2$CF$_2$O)$_b$—;
—(C$_3$F$_6$O)$_r$—(C$_2$F$_4$O)$_b$—(CFL$_0$O)$_t$—;
from the monofunctional ones (1=1):
(C$_3$F$_6$O)$_r$—(CFL$_0$O)$_t$—; wherein L$_0$ and the a, b, r, t indexes have the above mentioned value, still more preferably —(CF$_2$O)$_a$—(CF$_2$CF$_2$O)$_b$—

The compounds of formula (I) preferably used according to the present invention are those having L=(CH$_2$—CH$_2$O)$_n$ with n=1–3; Z$_1$ equal to or different from Z$_2$ is selected from H, NH$_4$, or an alkaline metal cation; 1=2.

The compounds of general formula (I), having the following formulas, are still more preferred:

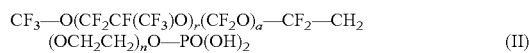

wherein r/a=0.5–2.0 and n=1–2;

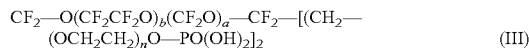

wherein b/a=0.5–3.0 and n=1–2; wherein a, b and r have the above mentioned meaning.

The component B) is preferably selected from: ethanol, ethylene glycol, isopropanol, propanol, acetone, methoxy-ethanol, propylene glycol, propan-1,2-diol, dimethoxy methane, methoxy-isopropanol, diethylene glycol, butan-1,4-diol, diethylene glycol monoethylenether, pentan-1,2-diol, diethylene glycol monoethylether, dipropylene glycol, dipropylene glycol monomethylether, dipropylene glycol monoethylether; still more preferably: ethanol, isopropanol and propylene glycol.

In the concentrated composition of the invention the amounts of each of the components A), B) and C) can range from 0.01% to 70% by weight of the composition, preferably from 20% to 40% by weight, the sum of A)+B)+C) being equal to 100% by weight of the composition.

Still more preferably the concentrated composition contains component A) in a percentage by weight in the range 20%–40%, component B) in the range 30–70% and water component C) in the minimum amount required to obtain a clear solution (the compound of formula (I) as such is insoluble in water), and component C) is generally in the range 5–30% by weight.

The composition of the invention appears as a monophase clear solution, stable in the time in environmental conditions at temperatures in the range from 10° C. to 35° C. also for long periods (6 months or more) of shelf storage.

Another object of the present invention is a process for preparing said concentrated compositions comprising the following steps:
  solubilization or dispersion with partial solubilization of a (per)fluoropolyether phosphate component A) in component B) at room temperature under mild stirring;
  addition under stirring, to the previous mixture of water component C) initially dropwise, so that component A) is not separated, by dispersing the drop so that the initial appearance of the solution is recovered before adding the subsequent ones, the water aliquots can be increased until the addition is completed, lastly obtaining a clear solution.

Surprisingly while the (per)fluoropolyether phosphate as such in unsoluble in water the mixture of the perfluoropolyether phosphate with component B) is instead dilutable with water to form, as said, a clear solution.

The added water is preferably at a temperature in the range 50° C.–60° C.

Another object of the present invention is the use of the concentrated compositions of the invention for the preparation of cosmetic compositions under the form of solutions, gels, emulsions, pastes and aerosols or serviettes impregnated with said cosmetic compositions for the skin protection against irritating agents, for the hair protection and treatment, for the protection against sun radiations, for detergency, as deodorants, after-shaves, disinfectants for external use, make-up compositions and for the nail-varnish removal.

To formulate the cosmetic compositions, the concentrated compositions of the present invention are diluted with the necessary solvents and excipients so that the final percentage by weight of the (per)fluoropolyether phosphate is in the range 0.01–10%, preferably 0.5–5%.

The concentrated composition can for example be diluted to form a homogeneous solution. In this case the dilution solvent is for example selected from water, acetone, linear or branched alcohols from 2 to 3 carbon atoms and their corresponding methyl ethers; linear or branched glycols from 2 to 6 carbon atoms and their corresponding monoalkylethers wherein the linear or branched ether alkyl group has a number of carbon atoms from 1 to 4; dimethoxymethane.

Preferably the diluent is water or it is formed by mixtures of water with one or more of the other above mentioned solvents or diluents.

To said final solution the excipients well known to the skilled man, such as perfumes, dyes, etc., can be added.

The concentrated composition can also be directly added to an already formulated hydrophilic gel, obtaining protective gels. The hydrophilic gelling agents can for example be selected from polysaccharides, such as cellulose derivatives, xanthan rubber, carruba rubber and alginates; acrylic derivatives, such as carbomer, glyceropolyacrylates and polymethacrylates; mineral and synthetic silicates; inorganic salts such as sodium chloride or magnesium sulphate.

Said protective gels can comprise other ingredients or excipients well known to the skilled man, such as pigments, sun filters, emollient oils (including non functionalized perfluoropolyethers), surfactants.

The concentrated composition of the present invention can be added to emulsions of the oil/water, or water/oil type or to gel emulsions based on acrylic polymer emulsifiers such as PEMULEN® (acrylates/C10–30 alkyl acrylate cross polymer) TR-1 or PEMULEN® TR-2, obtaining stable emulsions. Said emulsions are considered stable since no separation of phases both after conditioning for 60 days in stove at the temperature of 40° C., and after centrifugation at 4,000 rpm for 10 minutes, occurs.

Other cosmetic compositions can be prepared by formulating the concentrated composition object of the present invention with suitable carriers and excipients well known to the skilled man in order to obtain soaps, syndet (synthetic soaps) or mixtures thereof; shampoos, preferably containing non ionic and anionic surfactants; tooth pastes.

For the evaluation of the protective hydro and oil-repellent activity, absorption tests have been carried out on filter paper treated with the concentrated composition of the present invention and of a cosmetic gel formulation obtained by said concentrated composition. See the Examples.

The (per)fluoropolyethers of general formula (I) are obtainable by the well known processes of the prior art, see for example the following patents herein incorporated by reference: U.S. Pat. Nos. 3,665,041, 2,242,218, 3,715,378, and EP 239,123. The functionalized fluoropolyethers having an hydroxyl termination are obtained for example according to EP 148,482, U.S. Pat. No. 3,810,874.

The preparation of the monofunctional (per)fluoropolyether phosphates of general formula (I) wherein $R_f$ has a perfluoroalkyl end group can be carried out by reacting the corresponding monohydroxy-terminated (per)fluoroalkylene oxides with $POCl_3$. A molar ratio $POCl_3$/hydroxy-terminated compound in the range 2/1–10/1, preferably 6/1–8/1 is used. The reaction is carried out by slowly dropping the monohydroxy-terminated (per)fluoropolyether in $POCl_3$, at a temperature in the range 50°–100° C., preferably 70°–80° C., by eliminating the HCl vapours in a KOH trap. The $POCl_3$ excess is removed by distillation while the formed adduct is hydrolyzed by $H_2O$. The hydrolyzed adduct is further reacted for example with an equimolar amount of hydroxy-terminated (per)fluoropolyether to form the ester.

The separation of the obtained product is carried out by extraction with a suitable organic solvent, such as for example ethyl acetate. From the organic phase the compound of formula (I) is separated according to known techniques, for example by the solvent evaporation.

The preparation of bifunctional (per)fluoropolyether phosphates (in this case $R_f$ of formula (I) has no perfluoroalkyl end groups) can be carried out by reacting the corresponding di-hydroxy-terminated (per)fluoroalkylenoxides with $POCl_3$. A molar ratio $POCl_3$/di-hydroxy-terminated compound in the range 4/1–20/1, preferably 12/1–16/1, is used. The reaction is carried out by slowly dropping the hydroxy-terminated compound in $POCl_3$, at a temperature in the range 50°–100° C., preferably 70°–80° C., by eliminating the HCl vapours in a KOH trap. The $POCl_3$ excess is removed by distillation while the formed adduct is hydrolized by $H_2O$. The separation of the product is carried out by extraction with an organic solvent, such as for example ethyl acetate. From the organic phase the product is separated according to known techniques, for example by solvent evaporation.

Some examples are reported hereinafter, but they are not limitative of the present invention.

EXAMPLE 1

50 g of bifunctional perfluoropolyether phosphate chemically defined as polyperfluoroethoxymethoxydifluoroethyl PEG phosphate (FOMBLIN® HC/P2-1000 (perfluoropolyether phosphate)), having number average molecular weight of the perfluorinated chain of about 1,000, are solubilized, under slow stirring, in 100 g of ethanol. To this solution 50 g of water, initially drop by drop, are subsequently added, stopping the addition if turbidity appears in the solution and in this case by mixing until turbidity disappears. After few drops, the amount of water which is each time added is increased, maintaining the solution under stirring. At the end a limpid, transparent solution, having the following composition as percentage by weight is obtained:
FOMBLIN® HC/P2-1000 (component A): 25%
Ethanol (component B): 50%
water (component C): 25%.

EXAMPLE 2

One operates as in Example 1, but replacing ethanol with propylene glycol.
A limpid, transparent solution, having the following composition as percentage by weight is obtained:
FOMBLIN® HC/P2-1000 (component A): 25%
Propylene glycol (component B): 50%
water (component C): 25%.

EXAMPLE 3 COMPARATIVE (COMP)

A concentrated composition is prepared as in Example 1, by mixing component A) with component B), but omitting the addition of component C).
A limpid solution having the following composition is obtained:
FOMBLIN® HC/P2-1000 (component A): 33.3%
Ethanol (component B): 66.6%

EXAMPLE 4 COMPARATIVE (COMP)

50 g of bifunctional perfluoropolyether having hydroxyl end groups, chemically defined as poliperfluoroethoxymethoxydifluorohydroxyethyl PEG ether, FOMBLIN® HC/OH-1000 (perfluoropolyether diol) having a number average molecular weight of the perfluorinated chain of about 1,000, are solubilized in 100 g of ethanol. A transparent solution is obtained, to which 50 g of water are added in aliquots at 50° C. under continuous stirring, as indicated in Example 1.
The composition as percentage by weight is the following:
FOMBLIN® HC/OH-1000 (component A): 25%
Ethanol (component B): 50%
water (component C): 25%.
The immediate separation of the bifunctional perfluoropolyether from the aqueous phase is observed with formation of a lower phase.
This Example shows that a bifunctional (per)fluoropolyether having hydroxyl end groups cannot be used for preparing the concentrated compositions of the present invention.

EXAMPLE 5

Dilution with Water of the Concentrated Solution According to Example 1.
One operates as in Example 1, further diluting the obtained composition with water until a final solution having a 3% concentration by weight of FOMBLIN® HC/P2-1000 is obtained.
Said solution appears homogeneous and limpid as the starting one. This shows that the concentrated solutions according to the present invention are dilutable by using the previously described solvents.

EXAMPLE 6

Hydro/Oil-Repellence Test on the Solutions of Examples 3 (Comparative) and 5 and on a Non Functionalized Perfluoropolyether as Such.
0.5 ml of the solutions of Example 3 (comparative) and of Example 5 have been applied on a filter paper by distributing each of the two liquids on an area of 20 cm². The area is delimited with a marking pen and the paper dried by a hot air flow. A drop of vaseline oil and water respectively are applied on separated parts of the area treated with each solution, measuring the absorption times of the paper.

The part treated with the solution at 3% by weight of FOMBLIN® HC/P2-1000 absorbs the water drop in a time higher than 1 hour and the oil drop in a time higher than 6 hours.

The part treated with the solution of Example 3 (comparative) absorbs the water drop in a time lower than 20 minutes, while for the absorption of the oil drop the results are similar to those above described treating the paper with the diluted solution according to the invention of Example 5.

The filter paper has been treated with the same above described procedures with the non functionalized perfluoropolyether polyperfluoromethylisopropyl ether FOMBLIN® HC/04, measuring the hydro-/oil-repellence by the above described procedure. The perfluoropolyether is used pure being it unsoluble either in component B) or in component C) of the composition according to the present invention.

The absorption times in this case are higher than 1 hour for the water and lower than 20 minutes for the oil.

This test shows that both a concentrated composition of the perfluoropolyether phosphate wherein water is absent, and a non functionalized perfluoropolyether as such, have not the combination of hydro-repellence and oil-repellence properties of the diluted compositions of the present inventions.

EXAMPLE 7

One operates as in Example 1, diluting with a mixture water/ethanol so as to obtain a 5% solution by weight of FOMBLIN® HC/P2-1000 and 25% by weight of ethanol. The final solution has pH 2.01 and it appears limpid and homogeneous as the starting one. The pH is then increased of about a pH unit a time, by adding each time some drops of a concentrated NaOH solution, keeping an aliquot of about 100 ml of each solution having the correct pH.

At the end 5 different solutions each having the pH indicated in Table 1, are obtained, in addition to the starting one. On these solutions the hydro-/oil-repellence test is carried out by operating as described in Example 6.

The results are indicated in Table 1 and show that when the composition of the invention contains alcohol as component B), a good combination of hydro-/oil-repellence properties is obtained at low pH values, to which the perfluoropolyether phosphoric functionality is not neutralized or is only partially neutralized.

EXAMPLE 8

Cosmetic Composition Usable as Nail-Varnish.

5 g of diethylene glycol monoethylether and 93 g of acetone are added to 2 g of the concentrated mixture of Example 1. A limpid homogeneous solution, usable as solvent for nail varnish is obtained, having the following composition (% by weight).

| perfluoropolyether phosphate (FOMBLIN ® HC/P2-1000) | 0.5 |
|---|---|
| ethanol | 1 |
| water | 0.5 |
| diethylenglycol monoethylether | 5 |
| acetone up to | 100 |

EXAMPLE 9

Cosmetic Composition Usable as Collutory.

2 g of ethanol, 10 g of glycerine, isopropyl methacresol (timol) are added to 2 g of the concentrated mixture of Example 1, adding an amount of water until obtaining 100 g of solution.

The % composition by weight is the following:

| isopropyl methacresol (timol) | 0.03 |
|---|---|
| perfluoropolyether phosphate (FOMBLIN$^R$ HC/P2-1000) | 0.5 |
| ethanol | 3.0 |
| glycerine | 10.0 |
| aroma | as suff. |
| water up to | 100 |

EXAMPLE 10

Dilution with Water of the Concentrated Solution of Example 2.

Starting from the concentrated composition prepared in Example 2, water is added until obtaining a final solution containing 3% by weight of FOMBLIN® HC/P2–1000. The solution has pH 2.38 and it appears homogeneous and limpid.

EXAMPLE 11

Cosmetic Composition Usable as Protective Gel.

The concentrated solution of Example 1 is mixed with a gel obtained by adding to Carbomer in powder an amount of water and neutralizing with NaOH. The excipients mentioned hereunder are then added, obtaining the following composition as % by weight:

| Carbomer (CARBOPOL ® Ultrez 10) (carbomer)) | 1.0 |
|---|---|
| perfluoropolyether phosphate (FOMBLIN ® HC/P2-1000) | 5 |
| ethanol | 5.0 |
| dye CI 42051 | 0.05 |
| phenoxyethanol + methylparaben + propylparaben | 0.6 |
| sodium hydroxide | 0.4 |
| water up to | 100 |

A blue, transparent gel having pH 5.2 is obtained. The viscosity, measured by a Brookfield DV II viscometer, 10 rpm, at 25° C. is 28,000 mPa·s.

The gel kept in the packing is stable at the shelf storage for times higher than 6 months at room temperature.

EXAMPLE 12

Protective gel.

A gel is prepared according to the procedure of the previous Example but increasing the ethanol amount from 5% to 25%. The dye is not included in the formulation. The following composition as % by weight is obtained:

| Carbomer (CARBOPOL ® Ultrez 10) | 1.2 |
|---|---|
| perfluoropolyether phosphate (FOMBLIN ® HC/P2-1000) | 2.0 |
| ethanol | 25.0 |
| sodium hydroxide | 0.45 |
| water up to | 100 |

A transparent gel having pH 6.1 and a viscosity, measured as indicated in Example 11, of 45,300 mPa·s is obtained.

EXAMPLE 13

Protective Gel.

The procedure described in Example 11 is followed, omitting the neutralization and using as gelling excipient xanthan rubber. The obtained composition is the following as percentage by weight:

| | |
|---|---|
| xanthan rubber (RHODICARE ® T (xanthum gum)) | 1.3 |
| perfluoropolyether phosphate (FOMBLIN ® HC/P2-1000) | 5 |
| ethanol | 25.0 |
| water up to | 100 |

A transparent gel having pH 2.8 and a viscosity of 13,400 mPa·s measured as described in Example 11, is obtained.

EXAMPLE 14

Hydro-/Oil-Repellence Test on the Gel Formulations of Examples 11, 12 and 13 Respectively.

The process described in Example 6 is followed, but applying on the paper 0.5 ml of each gel.

For comparative purpose the commercial cream DECU-BAL® (hand barrier cream made of water, cetearyl alcohol, isopropyl mirystate, sorbitan stearate, dimethecone (silicone oil), polysorbate 60, sorbic acid) (produced by A/S Dumex of Copenaghen) having a high content of greases (38% by weight) has been used. The obtained results are indicated in Table 2.

The Table shows that the formulations according to the present invention have better oil-repellent properties than those of the commercial cream, while the hydro-repellent properties are equal or comparable, depending on the type of gel used, even though the composition of the invention contain an amount of the hydrophobic component (perfluoropolyether phosphate) which is about from 1/20 to 1/6 with respect to the total lipophilic (hydrophobic) amount (greases) of the commercial cream.

EXAMPLE 14a

In order to check whether the hydro-/oil-repellent properties of the cosmetic formulations according to the present invention are kept also under drastic conditions, two different portions of filter paper have been respectively covered with the cosmetic formulations according to Examples 11, 12 and 13 and with the comparative commercial cream, according to the procedure described in Example 6. For each formulation used, one of the two portions of the filter paper is dipped in hot running water at 70° C. for 10 minutes, the other one in water containing 0.5% by weight of liquid soap for 10 minutes, at room temperature. After drying, the hydro/oil-repellent properties are measured as described in Example 6. The results are reported respectively in Tables 3 and 4.

The Tables show that under the conditions adopted in the test the cosmetic formulations of the invention maintain the hydro-/oil-repellent properties while the hydro-repellence of the commercial cream results lowered.

EXAMPLE 15

Biphasic Cosmetic Formulation in Gel Form.

100 parts of the gel of Example 11 are additives with 3 parts of iron oxides, 3 parts of mica and 3 parts of talc obtaining a colored gel, which kept in the packing is stable at the shelf storage for times higher than 6 months at room temperature.

EXAMPLE 16

Biphasic Cosmetic Formulation Gel-Emulsion.

10 g of neopentyl glycol diethylhexanoate are added to 50 g of the gel of Example 11, under continuous stirring. A gel emulsion is formed which kept in the packing is stable at the shelf storage for times higher than 6 months at room temperature.

EXAMPLE 17

Cosmetic Formulations of Sun Cream (Gel-Emulsion).
a) Sun Cream with UV Filter of Chemical Type
One operates as in Example 13, by adding to the base hydroalcoholic solution of perfluoropolyether phosphate (FOMBLIN® HC/P2-1000) polyperfluoromethylisopropylether (FOMBLIN® HC/R), UV screening substances of chemical type (butylmethoxybenzoylmethane and octylmethoxycinammate) and the usual excipients.

A sun gel cream pH=3.5 having the following composition (% by weight) is obtained:

| | |
|---|---|
| xanthan rubber (RHODICARE ® T) | 1.3 |
| perfluoropolyether phosphate (FOMBLIN ® HC/P2-1000) | 2.0 |
| perfluoropolyether (FOMBLIN ® HC/R) | 1.0 |
| ethanol | 30.0 |
| butylmethoxybenzoylmethane | 1.0 |
| octylmethoxycinammate | 5.0 |
| perfume | 0.05 |
| water up to | 100 | b) Sun Cream with UV Filter of Physical Type
One operates as in Example 13 by adding to the concentrated hydro alcoholic solution of perfluoropolyether phosphate (FOMBLIN® HC/P2-1000), ethyl alcohol, polyperfluoromethylisopropylether (FOMBLIN® HC/R), an UV screening substance of physical type (titanium dioxide) and the usual excipients.

A sun gel cream pH=4.3 having the following composition (% by weight) is obtained:

| | |
|---|---|
| xanthan rubber (RHODICARE ® T) | .3 |
| perfluoropolyether phosphate (FOMBLIN ® HC/P2-1000) | 2.0 |
| perfluoropolyether (FOMBLIN ® HC/R) | 1.0 |
| ethanol | 30.0 |
| titanium dioxide | 2.0 |
| perfume | 0.05 |
| water up to | 100 | c) Sun Cream with a Mixture of UV Filters of Chemical+Physical Type
One operates as in Example 13 by adding to the concentrated hydroalcoholic solution of perfluoropolyether phosphate (FOMBLIN® HC/P2-1000), ethyl alcohol, polyperfluoromethylisopropylether (FOMBLIN® HC/R), W screening substances of chemical type (butylmethoxy-benzoylmethane and octylmethoxycinammate), an UV screening substance of physical type (titanium dioxide) and the usual excipients.

A sun gel cream pH=4.3 having the following composition (% by weight) is obtained:

| | |
|---|---|
| xanthan rubber (RHODICARE ® T) | 1.3 |
| perfluoropolyether phosphate (FOMBLIN ® HC/P2-1000) | 2.0 |
| perfluoropolyether (FOMBLIN ® HC/R) | 1.0 |
| ethanol | 30.0 |
| butylmethoxybenzoylmethane | 1.0 |
| octylmethoxycinammate | 5.0 |
| titanium dioxide | 2.0 |
| perfume | 0.05 |
| water up to | 100 |

EXAMPLE 18 COMPARATIVE (COMP)

Preparation of a Gel Emulsion Containing a Non Functionalized Perfluoropolyether and Evaluation of the Hydro-/Oil-Repellent Properties.

A gel emulsion with the following formulation has been prepared, wherein as non functionalized perfluoropolyether FOMBLIN® HC/R having number average molecular weight 3,200 and perfluoromethyl end groups has been used.

The composition in % by weight is the following:

| | |
|---|---|
| mineral oil | 10 |
| caprylic/capric triglyceride | 5 |
| perfluoropolyether (FOMBLIN ® HC/R) | 5 |
| cetearyl isononanoate | 5 |
| acrylate/alkyl-acrylate (PEMULEN ® TR-1) | 0.4 |
| triethanolamine | 0.3 |
| phenoxyethanol + methylparaben + propylparaben | 0.6 |
| water up to | 100 |

The hydro-/oil-repellence test has been carried out as described in Examples 6 and 14. In this case the absorption of the water and vaseline oil drops from the filter paper treated with the emulsion is immediate. Therefore the formulation containing the non functionalized perfluoropolyether has no hydro-/oil-repellent properties.

EXAMPLE 19

Cosmetic Formulation Shampoo Type.

The solution at 25% by weight of perfluoropolyether phosphate (FOMBLIN® HC/P2-1000) of Example 2 is added of the following substances:

- surfactants: sodium laurylether sulphate (SLES, solution at 30% by weight in water), cocaminopropylbetaine (CAPB, solution at 20% by weight in water) and lauryl polyglucoside (LPG, solution at 20% by weight),
- viscosity improving agent: polyethylene glycol glyceryl cocoate with 7 molecules of ethylene oxide (polyethylene glycol (7) glyceryl cocoate, PEG-7 GC), obtaining a clear detergent composition pH 9.5 having the following composition (% by weight):

| | |
|---|---|
| sodium laurylether sulphate (SLES) | 3.5 |
| cocaminopropylbetaine (CAPB) | 1.5 |
| lauryl polyglucoside (LPG) | 5 |
| polyethylenglycol (7) glycerylcocoate | 0.5 |
| perfluoropolyether phosphate (FOMBLIN ® HC/P2-1000) | 1 |
| water up to | 100 |

EXAMPLE 20

Cosmetic Formulation Shampoo Type.

The previous Example is repeated without adding CAPB and using as viscosity improving agents, instead of polyethylene glycol 7 glyceryl cocoate, sodium chloride at 2% by weight in water and polyethylene glycol glyceryl oleate/cocoate with 18 molecules of ethylene oxide (PEG-18-glyceryl oleate/cocoate) at 3% by weight in water. A clear detergent formulation pH 8 having the following composition (% by weight) is obtained:

| | |
|---|---|
| sodium laurylether sulphate (SLES) | 3.5 |
| lauryl polyglucoside (LPG) | 5 |
| sodium chloride | 2 |
| PEG-18-glyceryl oleate/cocoate | 3 |
| perfluoropolyether phosphate (FOMBLIN ® HC/P2-1000) | 1 |
| water up to | 100 |

EXAMPLE 21

Preparation of a Syndet Cosmetic Formulation.

3 g of the solution of Example 2 are added to 97 g of the ZETESAP® 813A (a composition made from sodium lauryl ether sulphate, sodium sulfosuccinate and starch) base by Zschinmmer & Schwarz, formed for 30–40% by laurylether sodium sulphate and sodium laurylsulphosuccinate, and furthermore containing starch and greasy substances. After gradual homogenization and extrusion a solid syndet is obtained.

EXAMPLE 22

Cosmetic Formulation Marseille Soap Type.

3 g of the solution of Example 2 are added to 97 g of the base suitable to obtain Marseille soaps, of common commercial availability. After gradual homogenization and extrusion a Marseille soap is obtained.

EXAMPLE 23

Cosmetic Formulation in Fluid Emulsion.

The solution of Example 2 is used as the base for preparing a fluid emulsion having the following composition (% by weight):

| | |
|---|---|
| stearate of the stearyl ethoxylate alcohol (5) | 4 |
| cetylstearic ethoxylate alcohol (21) | 2 |
| octyl palmitate | 10 |
| propylene glycol | 9 |
| cetylstearyl alcohol | 0.5 |
| phenoxyethanol + methylparaben + propylparaben | 0.8 |
| perfluoropolyether phosphate (FOMBLIN ® HC/P2-1000) | 3 |
| water up to | 100 |

An emulsion having pH 2.55 and viscosity 10,100 mPa·s, measured as described in Example 11, is obtained. The emulsion kept in the packing is stable at the shelf-storage for times higher than 6 months at room temperature.

EXAMPLE 24

Cosmetic Formulation Gel-Emulsion.

The solution of Example 2 is used as the base for preparing a fluid emulsion having the following composition (% by weight):

| | |
|---|---|
| acrylate/alkylacrylate polymer PEMULIN ® TR-2 | 0.2 |
| carbomer | 0.3 |
| octyl palmitate | 10 |
| propylene glycol | 9 |
| sodium hydroxide | 0.17 |
| phenoxyethanol + methylparaben + propylparaben | 0.8 |
| perfluoropolyether phosphate (FOMBLIN ® HC/P2-1000) | 3 |
| disodium ETDA | 0.1 |
| water up to | 100 |

An emulsion having pH 4.96 and viscosity 9,900 mPa·s, measured as described in Example 11, is obtained. The emulsion kept in the packing is stable at the shelf-storage for times higher than 6 months at room temperature.

EXAMPLE 25

Cosmetic Formulation Water Emulsion in Oil.

The solution of Example 2 is used as the base for the preparation of a fluid emulsion having the following composition (% by weight):

| | |
|---|---|
| vaseline | 15 |
| cetylstearic ethoxylate alcohol (21) | 1.8 |
| mineral oil | 6 |
| propylene glycol | 9 |
| cetylstearyl alcohol | 7.2 |
| phenoxyethanol + methylparaben + propylparaben | 0.7 |
| perfluoropolyether phosphate (FOMBLIN ® HC/P2-1000) | 3 |
| tocopheryl acetate | 0.15 |
| disodium EDTA | 0.12 |
| citric acid | 0.04 |
| water up to | 100 |

The obtained emulsion has pH=2.79 and viscosity 20,800 mPa·s, measured as described in Example 11. The emulsion kept in the packing is stable at the shelf-storage for times higher than 6 months at room temperature.

EXAMPLE 26

Cosmetic Formulation in Gel Having a Physiological pH.

A concentrated composition has been prepared by mixing, according to the procedures described in Example 1, propylene glycol, FOMBLIN® HC/P2-1000 and water so as to obtain the following concentrated composition (percentages by weight):

| | |
|---|---|
| FOMBLIN HC/P2-1000: | 25% |
| Propylene glycol: | 25% |
| water: | 50% |

The concentrated composition has been added to a preformed Carbomer gel, prepared as described in Example 11 so as to have the following composition by weight:

| | |
|---|---|
| Carbomer (CARBOPOL ® Ultrez 10) | 0.2 |
| perfluoropolyether phosphate (FOMBLIN ® HC/P2-1000) | 0.5 |
| propylene glycol | 0.5 |
| phenoxyethanol + methylparaben + propylparaben | 0.6 |
| sodium hydroxide as suff. to pH | 5.4 |
| water up to | 100 |

A transparent gel, which kept in the packing is stable at the shelf-storage for times higher than 6 months at room temperature, is obtained.

On the gel the hydro-/oil-repellence test has been carried out according to Example 6. The results are reported in Table 5.

EXAMPLE 27

Cosmetic Formulation in Gel Having a Physiological pH

By using the concentrated composition prepslred in Example 26, three cosmetic formulations are prepared under the form of gels with xanthan rubber, having pH respectively of 4.5, 5.5, and 7

| | |
|---|---|
| a) Gel pH 4.5 | |
| xanthan rubber (RHODICARE ® T) | 0.2 |
| perfluoropolyether phosphate (FOMBLIN ® HC/P2-1000) | 2.0 |
| Propylene glycol | 2.0 |
| Sodium hydroxide as suff. to pH | 4.5 |
| water up to | 100 |
| b) Gel pH 5.5 | |
| xanthan rubber (RHODICARE ® T) | 0.2 |
| perfluoropolyether phosphate (FOMBLIN ® HC/P2-1000) | 2.0 |
| Propylene glycol | 2.0 |
| Sodium hydroxide as suff. to pH | 5.5 |
| water up to | 100 |
| c) Gel pH 7 | |
| xanthan rubber (RHODICARE ® T) | 0.2 |
| perfluoropolyether phosphate (FOMBLIN ® HC/P2-1000) | 2.0 |
| Propylene glycol | 2.0 |
| Sodium hydroxide as suff. to pH | 7 |
| water up to | 100 |

On these preparations the hydro-/oil-repellence test has been carried out according to Example 6. The results are reported in Table 5.

The Table shows that by using the concentrated compositions according to the present invention it is possible to prepare cosmetic formulations having a physiological pH, i.e. in the range 4.5–7, having a very good combination of hydro-/oil-repellent properties.

TABLE 1

| pH of FOMBLIN ® solution | Water absorption times | Oil absorption times |
|---|---|---|
| 2.01 | >1 hour | >6 hours |
| 3.4 | >1 hour | >6 hours |
| 4.37 | 2 minutes | >6 hours |

TABLE 1-continued

| pH of FOMBLIN® solution | Water absorption times | Oil absorption times |
|---|---|---|
| 6.8 | 10 seconds | >6 hours |
| 7.39 | 5 seconds | >6 hours |
| 8.43 | 3 seconds | >6 hours |

TABLE 2

| Examples | Water absorption times | Oil absorption times |
|---|---|---|
| 11 | >20 minutes | >6 hours |
| 12 | >20 minutes | >6 hours |
| 13 | >1 hour | >6 hours |
| DECUBAL® (comp) | >1 hour | immediate |

TABLE 3

Hydro/oilrepellent properties after treatment with water at 70° C.

| Examples | Water absorption times | Oil absorption times |
|---|---|---|
| 11 | >1 hour | >6 hours |
| 12 | >1 hour | >6 hours |
| 13 | >1 hour | >6 hours |
| DECUBAL® (comp) | 20 minutes | immediate |

TABLE 4

Hydro/oilrepellent properties after treatment with water at 0.5% of liquid soap at room temperature

| Examples | Water absorption times | Oil absorption times |
|---|---|---|
| 11 | >1 hour | >6 hours |
| 12 | >1 hour | >6 hours |
| 13 | >1 hour | >6 hours |
| DECUBAL® (comp) | 20 minutes | immediate |

TABLE 5

| Examples | Water absorption times | Oil absorption times |
|---|---|---|
| 26 | >2 hours | >6 hours |
| 27 a) | ~4 hours | >6 hours |
| 27 b) | ~4 hours | >6 hours |
| 27 c) | ~3 hours | >6 hours |

The invention claimed is:

1. Compositions comprising the following components:
A) a fluoropolyether phosphate of general formula:

$$R_f\text{—}[CF_2CH_2\text{—}O\text{—}L\text{—}P(O)(OZ_1)(OZ_2)]_I \quad (I)$$

wherein I=1 or 2;
L is a bivalent linking group;
$Z_1$ and $Z_2$ are equal to or different from each other, and each is independently selected from H, alkaline or ammonium cation, di- or tri-alkanolammonium cation wherein alkanol comprises from 1 to 20 C atoms, di- or tri- or tetra-alkylammonium cation wherein alkyl comprises from 1 to 20 C atoms, or $R_f\text{—}CF_2CH_2\text{—}O\text{—}L$;

$R_f$ is a fluoropolyether or perfluoropolyether chain comprising one or more repeating units selected from the group consisting of:
a) —$(C_3F_6O)$—;
b) —$(CF_2CF_2O)$—;
c) —$(CFL_0O)$—, wherein $L_0$=—F, —$CF_3$;
d) —$CF_2(CF_2)_{z'}CF_2O$—, wherein z' is an integer 1 or 2;
e) —$CH_2CF_2CF_2O$—;
when $R_f$ is monofunctional (I=1), an end group is of the perfluoroalkyl type selected from $CF_3O$, $C_2F_5O$, $C_3F_7O$; optionally a fluorine atom in the perfluoroalkyl end groups is substituted by a chlorine or hydrogen atom;
B) a solvent selected from the group consisting of: linear or branched alcohols from 2 to 3 carbon atoms and their corresponding methyl ethers; linear or branched glycols from 2 to 6 carbon atoms and their corresponding mono alkylethers wherein the linear or branched ether alkyl group comprises from 1 to 4 carbon atoms; and dimethoxy methane acetone; and
C) water.

2. Compositions according to claim 1, wherein in the compound of general formula (I), $Z_1$ and $Z_2$ are different from $R_f\text{—}CF_2CH_2\text{—}O\text{—}L$.

3. Compositions according to claim 1, wherein $R_f$ is of fluoropolyether type and it is optionally selected from one of the following structures:
1) —$(CF_2O)_a$—$(CF_2CF_2O)_b$—
with b/a in the range 0.3–10, extremes included, a being an integer different from 0;
2) —$(CF_2$—$(CF_2)_{z'}$—$CF_2O)_{b'}$—
wherein z' is an integer equal to 1 or 2;
3) —$(C_3F_6O)_r$—$(C_2F_4O)_b$—$(CFL_0O)_t$—,
with r/b=0.5–2.0 (r+b)/t=10–30, b and t being integers different from 0;
4) —$(OC_3F_6)_r$—$(CFL_0O)_t$—$OCF_2$—$R'_f$—$CF_2O$—$(C_3F_6O)_r$—$(CFL_0O)_t$—
5) —$(CF_2CF_2CH_2O)_{q'}$—$R'_f$—$O$—$(CH_2CF_2CF_2O)_{q'}$—
wherein:
$R'_f$ is a fluoroalkylene group from 1 to 4 carbon atoms;
$L_0$ is selected between F, $CF_3$;
6) —$(C_3F_6O)_r$—$OCF_2$—$R'_f$—$CF_2O$—$(C_3F_6O)_r$—
wherein in said formulas:
—$(C_3F_6O)$— can represent units of formula
—$(CF(CF_3)CF_2O)$— or —$(CF_2$—$CF(CF_3)O)$—
and a, b, b', q', r, t, are integers, whose sum is such that $R_f$ has a number average molecular weight $\overline{M}_n$, values in the range of about 300 and about 5,000.

4. Compositions according to claim 3, wherein the fluoropolyether chain $R_f$ is selected from the following structures:
—$(CF_2O)_a$—$(CF_2CF_2O)_b$—;
—$(C_3F_6O)_r$—$(C_2F_4O)_b$—$(CFL_0O)_t$—;
—$(C_3F_6O)_r$—$(CFL_0O)_t$—;
wherein $L_0$ and the a, b, r, t indexes have the above mentioned value.

5. Compositions according to claim 3, wherein the fluoropolyether chain $R_f$ is —$(CF_2O)_a$—$(CF_2CF_2O)_b$— and the a and b indexes are as above indicated.

6. Compositions according to claim 1, wherein the component A is a fluoropolyether having the following formulas:

$$CF_3\text{—}O(CF_2CF(CF_3)O)_r(CF_2O)_a\text{—}CF_2\text{—}CH_2 \\ (OCH_2CH_2)_nO\text{—}PO(OH)_2 \quad (II)$$

wherein r/a=0.5–2.0 and n=1–2;

$$CF_2\text{—}O(CF_2CF_2O)_b(CF_2O)_a\text{—}CF_2\text{—}[CH_2\text{—} \\ (OCH_2CH_2)_nO\text{—}PO(OH)_2]_2 \quad (III)$$

wherein b/a=0.5–3.0 and n=1–2; wherein a, b and r have the above mentioned meaning.

7. Compositions according to claim 1, wherein component B) is selected from: ethanol, ethylene glycol, isopropanol, propanol, acetone, methoxyethanol, propylene glycol, propan-1,2-diol, dimethoxy methane, methoxyisopropanol, diethylene glycol, butan-1,4-diol, diethylene glycol monoethylenether, pentan-1,2-diol, diethylene glycol monoethylether, dipropylene glycol, dipropylene glycol monomethylether, dipropylene glycol monoethylether.

8. Compositions according to claim 1, wherein the amounts of each of the components A), B) and C) range from 0.01% to 70% by weight, the sum of A)+B)+C) being the 100% by weight of the composition.

9. Compositions according to claim 8, wherein the percentage by weight of component A) is in the range 20%–40%, that of component B) in the range 30–70% and water in the range 5–30%.

10. A process for preparing compositions according to claim 1, comprising:
   1) solubilization or dispersion with partial solubilization of a fluoropolyether phosphate component A) in component B) at room temperature under mild stirring;
   2) addition under stirring of water component C) initially dropwise, so that component A) is not separated from the solvent, dispersing the drop so that the initial appearance of the solution is recovered before adding the subsequent ones, the water aliquots are gradually increased until the addition is completed, obtaining a limpid solution.

11. Compositions according to claim 1 wherein alkanol comprises 1–4 C atoms or alkyl comprises 1–4 C atoms.

12. Compositions according to claim 2 wherein $Z_1=Z_2=H$ and I=2.

13. Compositions according to claim 3 wherein $\overline{M}_n$ values are in the range of 800–2,500.

14. Compositions according to claim 7 wherein component B) is selected from ethanol, isopropanol or propylene glycol.

15. Compositions according to claim 8 wherein the amounts of the components A), B) and C) range from 20% to 40% by weight.

16. Compositions according to claim 1 wherein L is $(CHR_1CHR_2O)_n$, wherein $R_1$ and $R_2$ are equal to or different from each other and are selected from H and $CH_3$; and n is an integer in the range of 1–50.

17. Compositions according to claim 16, wherein n is an integer in the range of 1–6.

18. Compositions according to claim 17, wherein the compounds of formula (I) are those having $L=(CH_2-CH_2O)_n$ with n=1–3; $Z_1$ equal to or different from $Z_2$ is selected from H, $NH_4$, or an alkaline metal cation; I=2.

* * * * *